United States Patent [19]

Dumont et al.

[11] Patent Number: 4,713,390

[45] Date of Patent: Dec. 15, 1987

[54] SULFURATED HYDANTOIN DERIVATIVES AND PHARMACEUTICAL COMPOSITIONS CONTAINING SAME

[75] Inventors: Pierre Dumont, Gembloux; Jacques Poupaert, Louvain-a-Neuve, both of Belgium

[73] Assignee: Region Wallonne, Brussels, Belgium

[21] Appl. No.: 821,736

[22] PCT Filed: Apr. 16, 1985

[86] PCT No.: PCT/BE85/00007

§ 371 Date: Dec. 20, 1985

§ 102(e) Date: Dec. 20, 1985

[87] PCT Pub. No.: WO85/05103

PCT Pub. Date: Nov. 21, 1985

[30] Foreign Application Priority Data

Apr. 27, 1984 [BE] Belgium .................................. 899531

[51] Int. Cl.$^4$ .................. C07D 235/30; A61K 31/415
[52] U.S. Cl. ..................................... 514/389; 548/308; 514/390

[58] Field of Search ................ 548/308; 514/389, 390

[56] References Cited

U.S. PATENT DOCUMENTS 4,230,709 10/1980 Jamieson et al. .................. 548/308

FOREIGN PATENT DOCUMENTS 2825245 6/1978 Fed. Rep. of Germany ...... 548/308

OTHER PUBLICATIONS

Poupaert et al., Eur. J. Med. Chem., Nov.-Dec., 1980-15, No. 6., pp. 511-514.

*Primary Examiner*—John M. Ford
*Assistant Examiner*—Robert C. Whittenbaugh
*Attorney, Agent, or Firm*—Sughrue, Mion, Zinn, Macpeak, and Seas

[57] ABSTRACT 5-(2-methyl-2-thiol ethyl) hydantoin and derivatives thereof are useful in the treatment of evolutive chronic polyarthritis.

7 Claims, No Drawings

SULFURATED HYDANTOIN DERIVATIVES AND PHARMACEUTICAL COMPOSITIONS CONTAINING SAME

The object of the present invention is new sulfurated hydantoin derivatives used for the basic treatment of rheumatoid arthritis or evolutive chronic polyarthritis. These substances seek to correct the chronic inflammatory response which is characterized by this infection and are very clearly distinguished from non-steroid anti-inflammatories, which reduce the acute inflammatory reaction during episodes of exacerbation without however stopping the progress of this disease.

For the treatment of such diseases it is known to clinically use antimalarial compounds, gold complexes and D-penicillamine.

This latter molecule has a well-established activity but is responsible for numerous secondary effects which limit its use and are the cause of abandonment during treatment.

The object of the present invention is new pharmaceutical products based on sulfurated derivatives of hydantoin and their uses in pharmaceutical compositions. Such compounds possess structural characteristics such that they provide a different development from that of D-penicillamine whilst maintaining comparable activity, thus providing the possibility of achieving lower toxicity and a better therapeutic index.

The new sulfurated derivatives of hydantoin in accordance with the invention are composed of a structure of general formula (I):

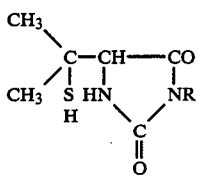

in which R represents a hydrogen atom, a lower alkyl group containing from 1 to 6 carbon atoms, a lower cycloalkyl group containing from 3 to 7 carbon atoms, or an aryl group with 6 carbon atoms. The new sulfurated derivatives of hydantoin also comprise their physiologically acceptable salts, their optical isomers, their mixtures and their racemic compounds. By physiologically acceptable salts are meant the salts obtained by the action of alkali or alkaline earth compounds in accordance with known methods or any other method described in the literature.

The claimed sulfurated derivatives of hydantoin have an asymmetric carbon at the 5 position, which gives them an optical activity. The optical isomers (enantiomers) which cover the compounds of the invention are conventionally designated by the symbols (R) and (S), or even by L and D, l and d, (+) or (−) or by combinations of said symbols.

When a specific designation has not been attributed to the compounds of the invention, these compounds designate both the individual enantiomers, their mixtures or their racemic compounds.

The pharmaceutical compositions of the present invention can comprise a single active hydantoin derivative or mixtures of several of said derivatives, taken in the broadest sense, and in particular comprising their salts and their optical isomers, their mixtures and their racemic compounds. The pharmaceutical compositions result from being placed in an appropriate form of administration, possibly with solid or liquid, inert, non-toxic vehicles and/or excipients which are used in galenic pharmaceutics. The choice of presentation of the compositions is carried out depending on whether it is to be administered orally, parenterally or by any other means. Thus, the galenic preparation may be in the form of tablets, pills, capsules, coated pills, drinkable or injectable solutions, or suppositories.

The unit dose used corresponds to a pharmacologically active dose established in accordance with methods which are well-known to one skilled in the art.

Among the new sulfurated derivatives of hydantoin used as active compounds in pharmaceutical compositions, the simplest derivative is obtained in the case of R=H, in general formula (I). In this case the compound is 5-(2-methyl 2-thiol ethyl) hydantoin.

The R substituent can be a lower alkyl group with 1 to 6 carbon atoms (methyl, ethyl, n-propyl, isopropyl, n-butyl, n-pentyl, n-hexyl). Preferably the methyl or ethyl group is selected. In such cases, the hydantoin derivatives are 3-methyl 5-(2-methyl 2-thiol) hydantoin and 3-ethyl 5-(2-methyl 2-thiol ethyl) hydantoin. The R substituent can be a lower cycloalkyl group containing from 3 to 7 carbon atoms selected from cyclopropyl, cyclobutyl, cyclopentyl, cyclohexyl and cycloheptyl. Preferably cyclohexyl is selected. In this case, the compound is 3-cyclohexyl 5-(2-methyl 2-thiol ethyl) hydantoin.

The R substituent can also be an aryl group selected with 6 carbon atoms, preferably the phenyl group. In this case, the resulting compound is 3-phenyl 5-(2-methyl 2-thiol ethyl) hydantoin.

The object of the present invention is also pharmaceutical compositions used as an immunomodulator and/or in the treatment of rheumatoid arthritis containing in a therapeutically effective quantity the new sulfurated derivatives of hydantoin responding to general formula (I). The claimed pharmaceutical products and the pharmaceutical compositions containing a therapeutically effective dose of said products manifest pharmacological activity comparable to that of D-penicillamine. It is surprising to note such activity. In effect, in spite of their relatively distant structure from that of D-penicillamine, the claimed compounds manifest high activity in the hypersensitivity test delayed with picryl chloride, (Taraye et al, *J. Pharm. Pharmacol.* 1980 32 584) which is presently considered as one of the most representative tests for the therapeutic activity of substances intended for the treatment of rheumatoid arthritis.

The products and pharmaceutical compositions of the invention do not show the anticonvulsive activity frequently encountered among the derivatives of the hydantoin nucleus and this is by application of the electroshock test. Finally, their acute toxicity, estimated with the $LD_{50}$ measurement on rodents is less than that of D-penicillamine. The synthesis method calls for a known method (Dakin reaction), but adapted to the requirements of stability.

The preparation of the active substances in accordance with the invention is described in a more detailed manner using the following examples, without however being limited to such.

EXAMPLE 1

Preparation of 5-(S)-(2-methyl 2-thiol ethyl) hydantoin

A solution of 30 g of D-penicillamine and 30 g of potassium cyanate in 100 ml of distilled and degassed water was heated to 80° C. for 30 minutes under a continuous current of nitrogen. The reaction mixture was then cooled in ice and acidified by means of 6N hydrochloric acid. The precipitate thus obtained was dried, washed with distilled water and placed in suspension in 600 ml of 3N hydrochloric acid. This was heated to 95° for 40 minutes. After cooling in ice, the crystalline product was dried and recrystallized in methanol:water. The resulting product, which was 5-(S)-(2-methyl 2-thiol ethyl) hydantoin, had a melting point of 247°–248° C. and an optical activity $(a)_{546} + 107°$ (concentration of 0.1 g in 100 ml of methanol).

EXAMPLE 2

Preparation of 3-(S)-methyl 5-(2-methyl 2-thiol ethyl) hydantoin 1 ml of pyridine at one time under agitation and 0.840 g of methyl isocyanate dropwise was added to a solution of 2 g of D-penicillamine and 0.536 g of NaOH in 20 ml of degassed distilled water cooled to 4° C.

The operation was carried out under nitrogen current. The reaction mixture was brought progressively to room temperature. After 24 hours, it was extracted twice with 20 ml of benzene or toluene. 20 ml of 6N hydrochloric acid was added to the aqueous phase and heated to 95° C. for 120 minutes. By cooling to room temperature, 1.6 g of a precipitate was obtained which was dried, washed with distilled water and dried under vacuum. After recrystallization in methanol:water, 3-(S)-methyl 5-(2-methyl 2-thiol ethyl) hydantoin was obtained whose melting point was 157°–158° C. and optical power $(a)_{546} + 104°$ (concentration of 0.1 g in 100 ml of methanol).

EXAMPLE 3

Preparation of 3-(R)-ethyl 5-(2-methyl 2-thiol ethyl) hydantoin

The same method was used as in Example 2, but substituting an equivalent quantity of ethyl isocyanate for the methyl isocyanate.

The product obtained was characterized by a melting point of 116°–118° C. and an optical activity of $(a)_{546} - 109°$ (concentration of 0.1 g in 100 ml of methanol).

EXAMPLE 4

Preparation of 3-(R,S)-cyclohexyl 5-(2-methyl 2-thiol ethyl) hydantoin

The same method was used as in Example 2, but substituting an equivalent quantity of cyclohexyl isocyanate for the methy isocyanate. The product obtained was characterized by a melting point of 156°–158° C.

EXAMPLE 5

Preparation of 3-(R,S)-phenyl 5-(2-methyl 2-thiol ethyl) hydantoin

The same method was used as in Example 2, but substituting an equivalent quantity of phenyl isocyanate for the methyl isocyanate.

The product obtained was characterized by a melting point of 109°–110° C.

EXAMPLE 6

Pharmaceutical composition for oral use 50 mg of one of the claimed compounds was dispersed in 200 mg of lactose and placed in a capsule of an appropriate format. In order to study the activity of the claimed compounds with regard to their immunomodulator properties, and more particularly with regard to their effects on cellular immunity, they were subject to the hypersensitivity test delayed with picryl chloride. This test was carried out on male mice of the NMRI strain of an average weight of 30 g. 10 animals were used for each product tested. Ten animals untreated with picryl chloride constituted a control batch and ten others a reference batch (animals treated with picryl chloride but not having received any claimed product). On day 1 the skin of the abdomen of the mouse was shaved. 0.1 ml of a 5% solution of picryl chloride in acetone was spread. On day 2 0.1 ml of a 1% suspension of gum tragacanth in distilled water containing the product to be tested was administered per os and per 10 g of body weight. The dose of the various products was 0.335 mole per kg. The control batch received the same volume of suspension of gum tragacanth. On day 3, the two surfaces of the right ear were treated with 5 µl of a 1% solution of picryl chloride in a 50:50 acetone-butyl phthalate mixture (challenge). These animals received the same product to be tested as on day 2, two hours before and two hours after the challenge. On day 4, the animals were killed by ether inhalation. The thickness of the external ear was measured in each of the animals. Activity was shown by a reduction of the swelling of the external ear as compared to a control batch. By way of example, the activity of the compounds 5-(S)-(2-methyl 2-thiol ethyl) hydantoin (compound 1) and 3-(S)-methyl 5-(2-methyl 2thiol ethyl) hydantoin (compound 2) compared to D-penicillamine is given.

TABLE I

| % of reduction in the swelling of the external ear of the NMRI mouse | |
|---|---|
| Batch treated by | % |
| Compound 1 | 80 |
| Compound 2 | 70 |
| D-penicillamine | 75 |

It is clearly shown from these tests that the sulfurated products claimed in the present invention manifest pharmacological activity of the D-penicillamine type; and this is in spite of their structure being considerably remote from that of said compound.

The claimed compounds no longer have the amino acid structure and therefore have a lesser chronic toxicity and a better therapeutic indication in the basic treatment.

What is claimed is:

1. A compound of the formula:

$$\begin{array}{c} CH_3 \\ \diagdown \\ C-CH-CO \\ \diagup \ | \ \ \ | \ \ \ \ | \\ CH_3 \ \ S \ \ HN \ \ \ \ NR \\ \ \ \ \ H \ \ \ \diagdown \diagup \\ \ \ \ \ \ \ \ \ \ \ C \\ \ \ \ \ \ \ \ \ \ \ \| \\ \ \ \ \ \ \ \ \ \ \ O \end{array}$$

wherein R represents a lower alkyl group containing from 1 to 6 carbon atoms, a lower cycloalkyl group containing from 3 to 7 carbon atoms, or an aryl group with 6 carbon atoms, as well as their physiologically acceptable salts, their optical isomers, their mixtures and their racemic compounds.

2. A compound of claim 1, wherein the R substituent is selected from among the methyl, ethyl, cyclohexyl or phenyl groups.

3. A compound of claim 1 selected from the group consisting of 3-methyl 5-(2-methyl 2-thiol ethyl) hydantoin, 3-ethyl 5-(2-methyl 2-thiol ethyl) hydantoin, 3-cyclohexyl 5-(2-methyl 2-thiol ethyl) hydantoin, 3-phenyl 5-(2-methyl 2-thiol ethyl) hydantoin, and their optical isomers, their mixtures and their racemic compounds.

4. A pharmaceutical composition for use as an immunomodulator and/or for the treatment of evolutive chronic polyarthritis comprising a therapeutically effect amount of a compound of any of claims 1 to 3, and a pharmaceutically acceptable carrier.

5. A pharmaceutical composition for use as an immunomodular and/or for the treatment of evolutive chronic polyarthritis comprising a pharmaceutically effective amount of 5-(2-methyl-2-thiol ethyl) hydantoin and a pharmaceutically acceptable carrier.

6. A process for treating evolutive chronic polyarthritis which comprises administering an effective amount of a compound of any one of claims 1 to 3.

7. A process for treating evolutive chronic polyarthritis which comprises administering a pharmaceutically effective amount of 5-(2-methyl-2-thiol ethyl) hydantoin.

* * * * *